(12) United States Patent
Takai et al.

(10) Patent No.: US 6,517,927 B2
(45) Date of Patent: *Feb. 11, 2003

(54) FLEXIBLE COMPOSITE SHEET

(75) Inventors: Hisashi Takai, Kagawa-ken (JP); Miou Suzuki, Kagawa-ken (JP)

(73) Assignee: Uni-Charm Corporation, Eheme-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/815,240

(22) Filed: Mar. 22, 2001

(65) Prior Publication Data

US 2001/0026861 A1 Oct. 4, 2001

(30) Foreign Application Priority Data

Mar. 31, 2000 (JP) .......................................... 2000-099023

(51) Int. Cl.[7] ................................................. A61F 13/15
(52) U.S. Cl. ........................ 428/167; 428/195; 428/196; 604/365; 604/385.01
(58) Field of Search ................................. 428/131, 132, 428/137, 138, 167, 195, 196; 604/378, 383, 365, 366, 367, 370, 371, 374, 385.01

(56) References Cited

U.S. PATENT DOCUMENTS

| 3,489,148 | A | * | 1/1970 | Duncan et al. | .............. 604/365 |
| 5,527,300 | A | | 6/1996 | Sauer | .......................... 604/378 |
| 5,607,760 | A | * | 3/1997 | Roe | .......................... 428/319.7 |
| 5,976,665 | A | | 11/1999 | Hansson | ..................... 428/136 |

FOREIGN PATENT DOCUMENTS

| EP | 0 788 874 A1 | 8/1997 |
| EP | 0 858 792 A2 | 8/1998 |
| EP | 0 919 212 A2 | 6/1999 |
| GB | 2 296 467 A | 7/1996 |
| JP | 11-217453 | 8/1999 |
| WO | WO 99/09923 | 3/1999 |

* cited by examiner

Primary Examiner—Nasser Ahmad
Assistant Examiner—Alicia Chevalier
(74) Attorney, Agent, or Firm—Baker & Daniels

(57) ABSTRACT

A composite sheet that includes a sheet-like fibrous assembly and a plurality of thermoplastic synthetic resin lamellae. Each of the film layer is formed on its upper surface with a plurality of grooves extending from one side edge to the other side edge of the film layer.

7 Claims, 5 Drawing Sheets

FLEXIBLE COMPOSITE SHEET

BACKGROUND OF THE INVENTION

This invention relates to a flexible composite sheet suitable for use as a liquid-pervious top material in a disposable body fluid absorbent sanitary article such as a disposable diaper, a sanitary napkin and the like.

Japanese Patent Application Publication No. 1999-217453A describes a flexible composite sheet comprising a sheet-like fibrous assembly having upper and lower surfaces and a flexible plastic sheet bonded to the upper surface of the fibrous assembly. The plastic sheet including a plurality of flat zones extending parallel one to another in one direction each having a thickness of 0.001~0.05 mm and a width of 0.03~1 mm and a plurality of opening arrays each defined between each pair of the adjacent flat zones and comprising a plurality of openings arranged intermittently in the one direction. Each pair of the adjacent flat portions with the opening array lying therebetween are connected to each other by bridge-like portions extending across the opening array. The respective flat portions include tooth-like portions extending upward from their upper surfaces. The upper surface of the fibrous assembly is exposed through the respective openings.

When the known composite sheet is used a top material to cover a liquid-absorbent core of an article, for example, a disposable diaper or a sanitary napkin, excretion such as urine, loose passage or menstrual discharge is apt to stay on the flat portions of the plastic sheet without being rapidly absorbed by the core.

SUMMARY OF THE INVENTION

It is an object of this invention to provide a composite sheet designed so that excretion discharged on such sheet may be rapidly absorbed by the core.

According to this invention, there is provided a flexible composite sheet comprising a sheet-like fibrous assembly having upper and lower surfaces and a plurality of thermoplastic synthetic resin lamellae each having an upper surface and a lower surface and being bonded to the upper surface of the sheet-like fibrous assembly so that the upper surface of the fibrous assembly is exposed through a gap defined between each pair of the adjacent lamellae.

The flexible composite sheet further comprises each of the lamellae being formed on the upper surface thereof with a plurality of grooves extending parallel one to another and each of the grooves extending from one side edge of the lamella to the other side edge of the same lamella opposed to the one side edge.

DETAILED DESCRIPTION OF THE PREFERRED EMBODIMENTS

Details of a flexible composite sheet according to this invention will be more fully understood from the description given hereunder with reference to the accompanying drawings.

Figure 1:
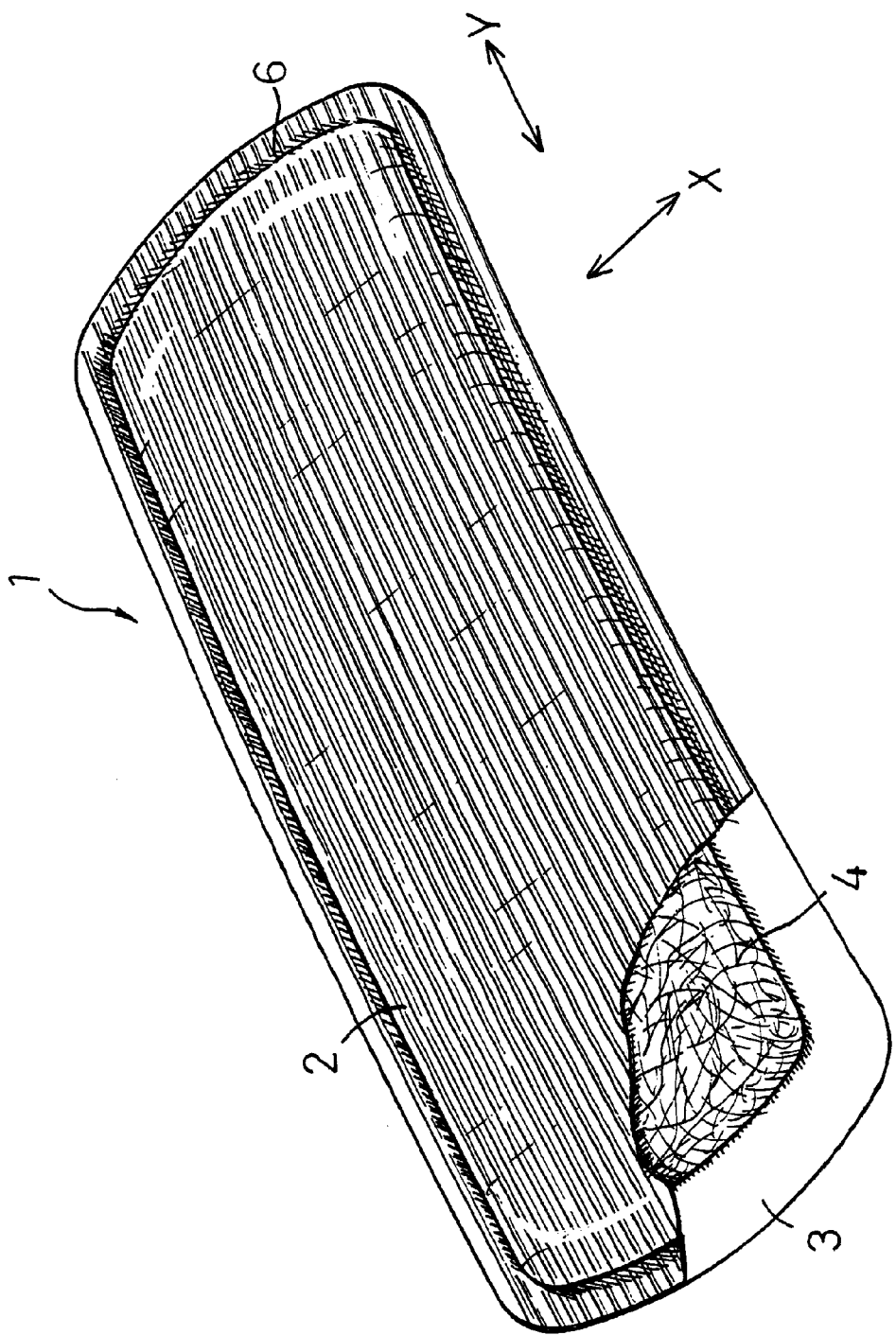
FIG. 1 is a perspective view depicting a partially cutaway sanitary napkin.

FIG. 1 is a perspective view depicting a sanitary napkin 1 as one embodiment of a disposable body fluid absorbent sanitary article according to this invention as partially broken away. The napkin 1 comprises a liquid-pervious topsheet 2, a liquid-impervious backsheet 3 and a liquid-absorbent core 4 disposed between these two sheets 2, 3 wherein portions of the topsheet 2 and the backsheet 3 extending outward beyond a peripheral edge of the core 4 are placed upon and fused with or bonded to each other. The napkin 1 has a width extending in X-direction and a length extending in Y-direction orthogonal to the X-direction. In this napkin 1, the flexible composite sheet is used as the topsheet 2.

Figure 2:
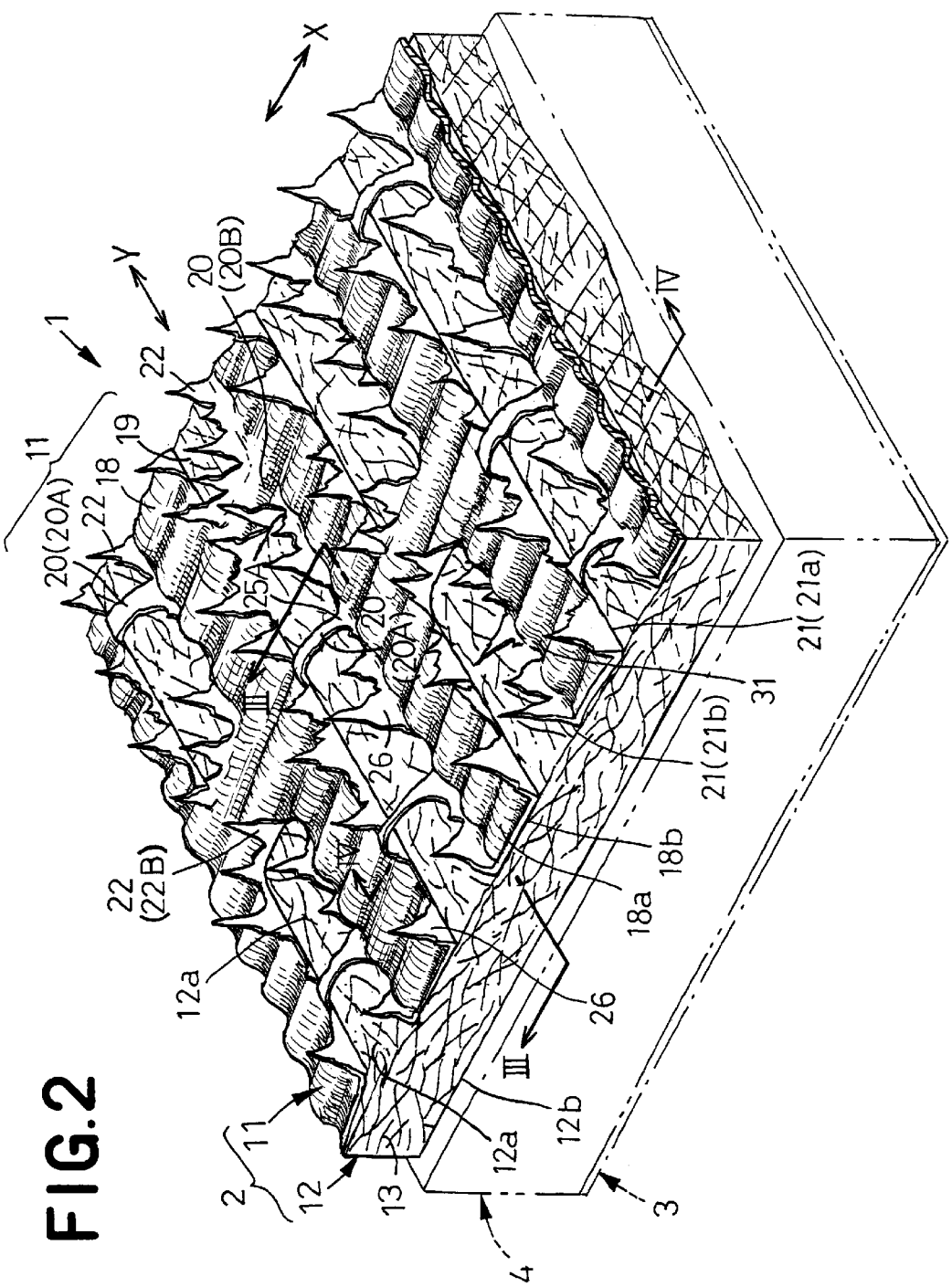
FIG. 2 is a fragmentary scale-enlarged perspective view depicting a part of FIG. 1.
Figure 3:
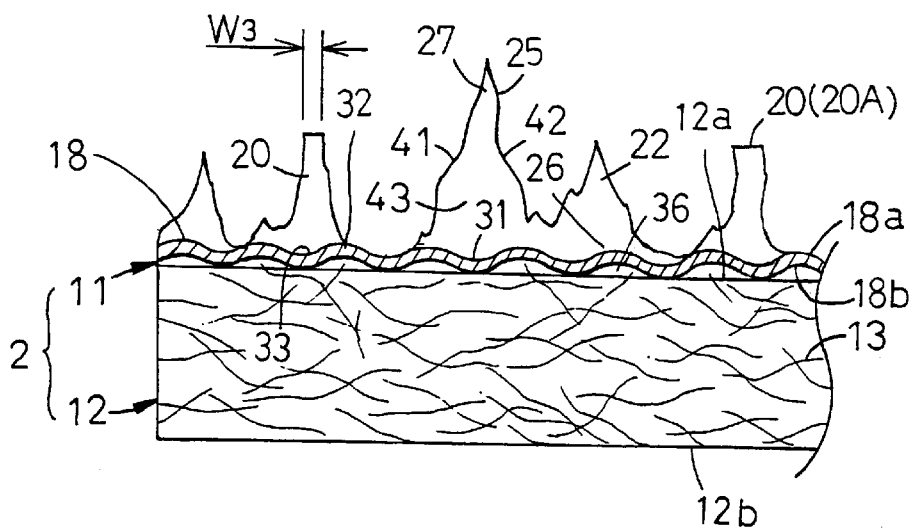
FIG. 3 is a sectional view taken along line III—III in FIG. 2.
Figure 4:
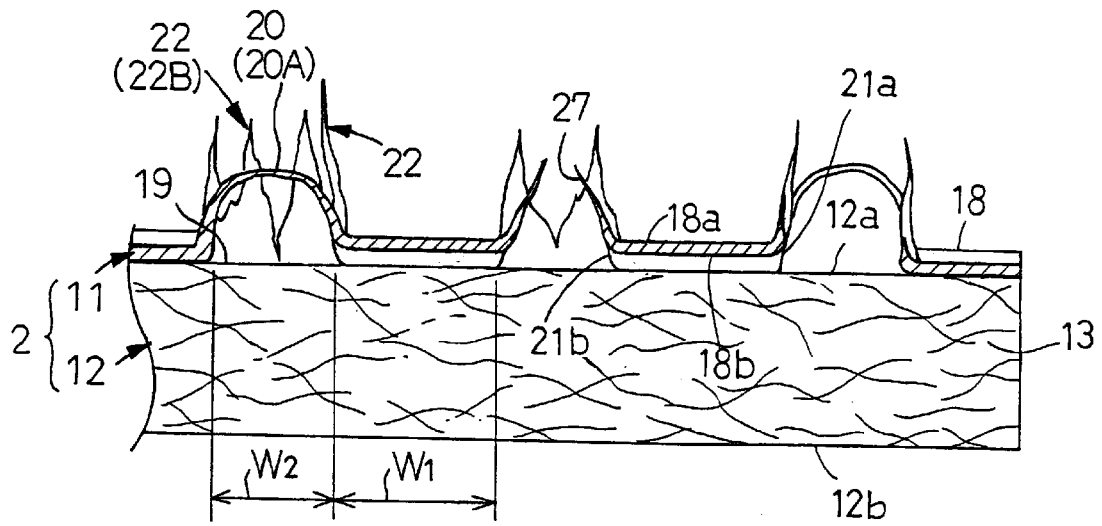
FIG. 4 is a sectional view taken along line IV—IV in FIG. 2.

FIG. 2 is a scale-enlarged fragmentary perspective view of the napkin 1 and FIGS. 3 and 4 are sectional views taken along lines III—III and IV—IV in FIG. 2, respectively. Referring to FIG. 2, the backsheet 3 and the core 4 are indicated by chain lines. The topsheet 2 corresponds to the flexible composite sheet according to this invention, which comprises a film layer 11 of thermoplastic synthetic resin defining the upper surface of the topsheet 2 and a nonwoven fabric layer 12 formed by an assembly of fibers 13. These two layers 11, 12 are bonded to or fused with each other. The film layer 11 has a plurality of ribbon-like lamellae 18 extending on the upper surface 12a of the nonwoven fabric layer 12 parallel one to another in the Y-direction, a plurality of openings 19 defined between each pair of the adjacent lamellae 18 and extending in the Y-direction, bridge-like portions 20 extending from directly opposed side edges 21 of each pair of the adjacent lamellae 18 across the openings 19 defined therebetween in the X-direction so as to connect the directly opposed side edges 21, and tooth-like portions 22 extending from the side edges 21 of the lamellae 18 upward as viewed in FIG. 2. The tooth-like portions 22 repeat irregular undulations in the Y-direction to describe a sawtooth wave.

The nonwoven fabric layer 12 has its upper surface 12a bonded to lower surface 18b of the lamella 18 and the upper surface 12a of the nonwoven fabric layer 12 is exposed through the openings 19.

The backsheet 3 is made of a thermoplastic sheet, a nonwoven fabric of thermoplastic synthetic fiber or a laminate of these sheet and a nonwoven fabric.

The core 4 is made of fluff pulp or a mixture of fluff pulp and superabsorption polymer.

The lamella 18 constituting the film layer 11 has its thickness of 0.001~0.05 mm as measured between the upper surface 18a and the lower surface 18b and a width $W_1$ of 0.03~5 mm as measured between each pair of the adjacent openings 19. Most of the openings 19 are relatively long in the Y-direction, preferably each having a width $W_2$ of 0.03~1 mm and a length corresponding to at least 1.5 times of the width $W_2$.

The lamella 18 is formed with a plurality of grooves 31 extending between the opposed side edges 21a, 21b of this lamella 18. These grooves 31 extend referably parallel one to another at an angle of 30~150° with respect to the Y-direction and each pair of the adjacent grooves 31 are preferably spaced apart from each other by a centerto-center distance of 0.03~10 mm. As will be apparent from FIG. 2, these grooves 31 are configured so that the lamella 18 curves so as to be convex from its upper surface 18a toward its lower surface 18b and has a thickness partially decreasing from the upper surface 18a toward the lower surface 18b, for example, in V-shape. A depth from a top 32 of lamella 18 lying between a pair of the adjacent grooves 31, 31 to a bottom 33 of the grooves 31 is in a range of 0.001~5 mm. While the lower surface 18b of the lamella 18 having the grooves 31 as shown in FIG. 3 is bonded to the upper surface 12a of the nonwoven fabric layer 12 at the bottoms 33 of the respective grooves 31, the lower surface 18b is spaced apart from the upper surface 12a of the nonwoven fabric layer 12 at regions defined between each pair of the adjacent bottoms 33, 33. In this manner, vacant spaces 36 are formed between these lower surface 18b and upper surface 12a. While opposite ends of the groove 31 are preferably in communication with the openings 19 along both of the opposite side edges 21a, 21b of the lamella 18, an alternative embodiment is also possible without departing from the scope of this invention in which one end of the groove 31 is in communication with the opening 19 along the side edge 21a or 21b but the other end lies at a proximal end 26 of the tooth-like portion 22 and is not in communication with the opening 19. Still another embodiment is also possible without departing from the scope of this invention in which there are provided the grooves 31 each having both ends lying at the proximal ends 26 of the tooth-like portions 26 and not in communication with the openings 19, in addition to the grooves 31 as have been described above.

The bridge-like portions 20 constituting the film layer 11 lie between each pair of the adjacent openings 19, 19 in the Y-direction and comprise the bridge-like portions 20A describing circular arcs which are convex upward from the lamellae 18 and the bridge-like portions 20B (See FIG. 2) horizontally extending along the nonwoven fabric layer 12. These bridge-like portions 20 preferably have a thickness equal to or less than the thickness of the lamellae 18 and a width $W_3$ (See FIG. 3) in the Y-direction at least of 0.001~2 mm.

Most of the tooth-like portions 22 constituting the film layer 11 are formed by a portion of the lamella 18 extending upward as viewed in the accompanying drawings from its opposite side edges 21a, 21b. Each of the tooth-like portions 22 has the proximal end 26 contiguous to the lamella 18 and a free end 27 extending upward from the proximal end 26. The tooth-like portion 22 is tapered from its proximal end 26 toward its free end 27 as best seen in a side sectional view of FIG. 3. An edge 25 of the tooth-like portion 22 repeats irregular undulations to form a sawtooth wave along the side edge 21a or 21b. The maximum height as measured from the lamella 18 to the edge 25 is preferably less than 1 mm to ensure a comfortable touch of the topsheet 2. Some of the tooth-like portions 22 designated by 22B may be formed along side edges of the bridge-like portions 20 (See FIG. 2).

The manner in which the edges 25 of the tooth-like portions 22 repeat irregular undulations is exemplarily depicted by FIG. 3. As will be seen in FIG. 3, the tooth-like portions 22 comprise irregularly contiguous triangular or substantially triangular regions 43 each defined by an oblique side 41 ascending substantially rightward, an oblique side 42 ascending substantially leftward and the proximal end 26 extending between these two oblique sides. The tooth-like portions 22B also may repeat such undulations. These tooth-like portions 22 inclusive of the tooth-like portions 22B have a thickness equal to or less than that of the lamella 18 so that these portions 22 may be flexibly deformed as they come in contact with the wearer's skin and thereby give the wearer velvet-like soft touch. While it is difficult to visually recognize the individual tooth-like portions 22, a plurality of the tooth-like portions 22 make the upper surface of the topsheet 2 look as napped. In addition, the tooth-like portions 22 diffusively reflect the light rays incident upon the topsheet 2, thereby advantageously alleviate a surface gloss peculiar to the plastic sheet and conceal the core stained with menstrual discharge.

The nonwoven fabric layer 12 may contain thermoplastic synthetic fiber by at least 70 wt % and hydrophilic chemical fiber such as rayon fiber and hydrophilic natural fiber such as cotton fiber or pulp fiber by at most 30 wt %. An example of the preferred nonwoven fabric layer 12 is of thermoplastic synthetic fiber having a fineness of 0.5~17 dtex and a basis weight of 5~50 g/m², for example, a thermal bond nonwoven fabric such as a spun bond nonwoven fabric, a point bond nonwoven fabric or an air-through nonwoven fabric, or a melt blown nonwoven fabric or a spun lace nonwoven fabric.

When the topsheet 2 obtained in this manner is used in the sanitary napkin 1, menstrual discharge is guided through the openings 19 and the nonwoven fabric layer 12 into the core 4. On the topsheet 2, menstrual discharge flows from the lamellae 18 first into the grooves 31 and then into the openings 19 and thereby an anxiety that an amount of menstrual discharge might stay on the lamellae 18 if the latters are flat can be remarkably alleviated. Particularly with the lamella 18 is convex upward between each pair of the adjacent grooves 31, 31, menstrual discharge necessarily flows into the grooves 31 without staying on the lamella 18 and an amount of the menstrual discharge which might stay on the lamella 18 is further decreased. The vacant spaces 36 defined between the convex portions of the lamella 18 and the nonwoven fabric layer 12 underlying the lamella 18 advantageously make the nonwoven fabric layer 12 stained with menstrual discharge less prominent. In this manner, the tooth-like portions 22 cooperate with the vacant spaces 36 to conceal stains of the used napkin 1 well enough. To improve such concealing effect, it is also possible to use plastics containing inorganic filler such as titanium oxide.

Figure 5:
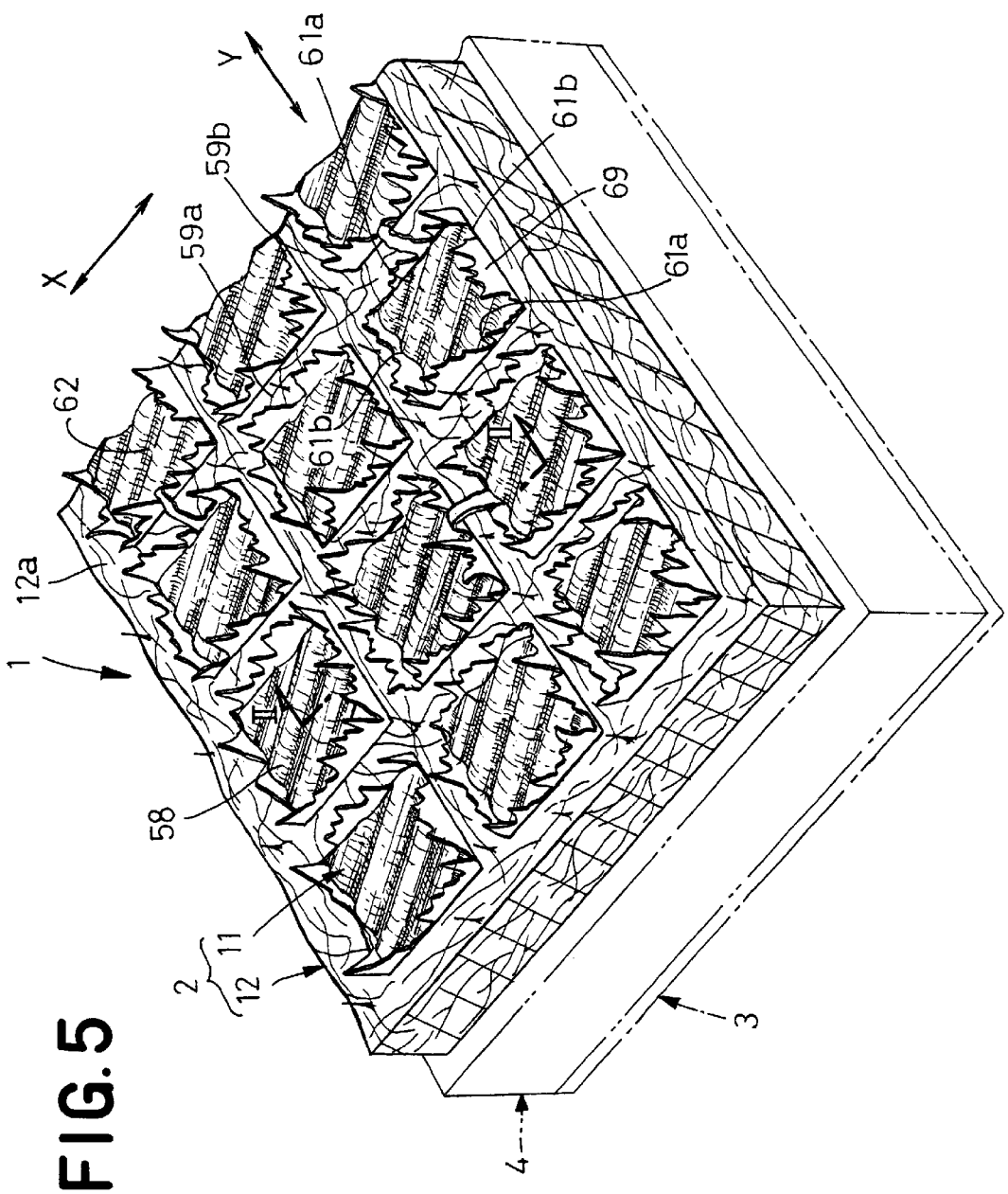
FIG. 5 is a view similar to FIG. 2 depicting another embodiment.

FIG. 5 is a view similar to FIG. 2 depicting another embodiment of this invention. This topsheet 2 also comprises the film layer 11 and the nonwoven fabric layer 12 but the film layer 11 comprises a plurality of substantially rectangular lamellae 58 and a plurality of openings 59a, 59b defined between each pair of the adjacent lamellae 58, 58 in the X-direction as well as in the Y-direction so that these openings 59a, 59b intersect each other. The upper surface 12a of the nonwoven fabric layer 12 is exposed through these openings 59a, 59b. Each of the lamellae 58 has side edges 61a, 61b extending along the openings 59a, 59b, respectively, which are, in turn, formed with a plurality of tooth-like portions 69. The lamellae 58 are formed with a plurality of grooves 62 extending between each pair of opposed side edges 61a, 61a; 61b, 61b and/or between each pair of adjacent and obliquely opposed side edges 61a, 61b. These grooves 62 are configured and function in the same manner as the grooves 31 shown in FIGS. 2~3 so that menstrual discharge can be rapidly guided into the openings 59a, 59b of the lamellae 58.

While the flexible composite sheet according to this invention has been described above with respect to the specific case in which the composite sheet is used as the topsheet 2 of the sanitary napkin 1, this composite sheet can be used as the liquid-pervious topsheet of the disposable body fluid absorbent article such as a disposable diaper or training pants. Furthermore, the composite sheet according to this invention is used as material for clothing such as a disposable gown on account of its touch and breathability.

Figure 6:
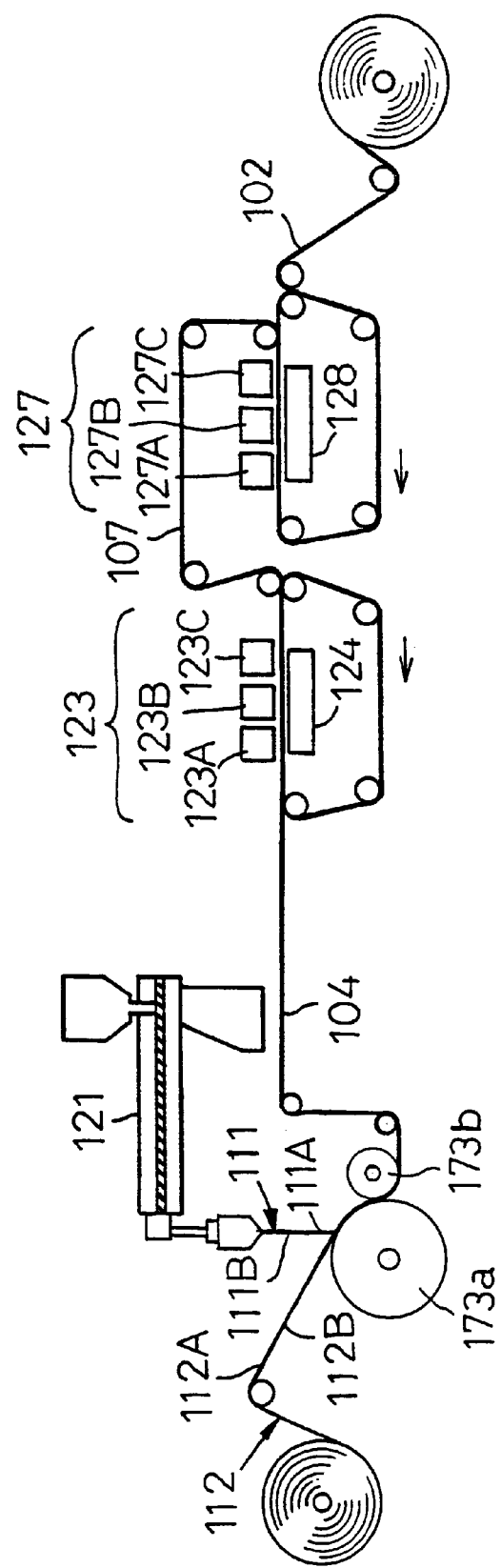
FIG. 6 is a diagram illustrating a process for making a composite sheet.

FIG. 6 is a diagram illustrating a process for continuously making a flexible composite sheet 102 destined to be used as the topsheet 2 of FIG. 2. From the left side as viewed in this diagram, the fibrous assembly in the form of second web 112 destined to be used as the nonwoven fabric layer 12 in FIG. 2 is continuously fed. First web 111 of thermoplastics destined to be used as the film layer 11 of the topsheet 2 is discharged from an extruder 121 in thermally molten state onto upper surface 112A of second web 112. These first and second webs 111, 112 are fed into a nip defined between a pair of compression rolls 173a, 173b in which these first and second webs 111, 112 are fused together to form first composite web 104.

A peripheral surface of the compression roll 173b is formed with a plurality of ridges and depressions (not shown) extending parallel one to another in a direction intersecting the direction in which the first web is fed so that these two webs 111, 112 may be compressed and fused along the heated ridges to form the grooves.

The first composite web 104 is fed to a first treating zone 123 in which high pressure columnar water streams are injected from a nozzle array 123A comprising a plurality of nozzles arranged at a desired pitch transversely of the first composite web 104 to upper surface 111A of the first web 111 to obtain second composite web 107. The first web 111 is selectively broken through by the columnar water streams and formed with openings arranged intermittently in the direction in which the second composite web 107 is fed. These openings are arranged parallel one to another transversely of the second composite web 107. In the first treating zone 123, second and third nozzle arrays may be provided, in addition to the single nozzle array, if desired to form a plurality of opening arrays. Specifically, columnar water streams may be injected also from the second and third nozzle arrays 123B, 123C, as illustrated. These nozzle arrays 123A, 123B, 123C are preferably arranged so that the nozzles of the respective arrays may have positions transversely of the second composite web 107 in alignment one with another longitudinally of the second composite web 107, i.e., loci of the high pressure columnar water streams ejected from the respective nozzles of the different three arrays may overlap one another. Below the first treating zone 123, there is provided a suction mechanism 124 adapted to collect injected water under a sucking effect.

The second composite web 107 is then fed to a second treating zone 127. In the second treating zone 127, there are provided nozzle arrays 127A, 127B1, 127C each comprising nozzles arranged transversely of the second composite web 107 and a suction mechanism 128. In this zone, The second web 112 of the second composite web 107 has its lower surface 112B subjected to the high pressure columnar water streams injected from the nozzle arrays and then dried to form the composite sheet 102. In the composite sheet 102, the component fibers of the first web 111 which has been selectively broken through in the first treating zone 123 are now oriented by the columnar water streams injected by the nozzles of the second treating zone 127 so as to extend the lower surface 111B toward the upper surface 111A of the first web 111. It is not essential that the loci of the water streams injected from the nozzle arrays 127A, 127B, 127C of the second treating zone 127 exactly coincide with the loci of the water streams injected from the nozzle arrays 123A, 123B, 123C of the first treating zone 123. However, the corresponding nozzles of the arrays in the first and second treating zones may be arranged substantially in coincidence with one another to ensure that the first web 111 can be broken through over a correspondingly large extent, i.e., relatively long openings can be formed, and most of the component fibers lying around the respective openings extend above the upper surface 111A of the first web 111. Such process for making the composite sheet advantageously facilitates the first web 111 to be selectively broken through at its predetermined region arranged transversely thereof whereby facilitates the plurality of opening arrays extending parallel to one another in the machine direction as well as the grooves each extending between each pair of the adjacent opening arrays to be formed.

Of the composite sheet 102, the first and second webs 111, 112 bonded together are destined to become the film layer 11 and the nonwoven fabric layer 12, the openings formed through the first web 111 are destined to become the openings 19 and the peripheral edges of the respective regions of the first web 111 selectively broken through are destined to define the tooth-like portions 22 in the topsheet 2 depicted in FIGS. 1~3. The regions of the first web 111 in the respective opening arrays arranged in the machine direction which have been left not broken through by the high pressure columnar water streams are destined to become the bridge-like portions 20 of the topsheet 2.

Each of the nozzle arrays 123A~123C; 127A~127C illustrated in FIG. 6 comprises the, nozzles, each having a diameter of 0.05~0.15 mm, arranged at an appropriate pitch. Preferably, water pressure of the columnar water stream is 3~20 MPa and a suction pressure of the suction mechanism is 2~20 KPa. In the first and second treating zones 123, 127, the webs to be treated are transported on the support conveyors 131, 132 such as the mesh screens.

The first web 111 and the second web 112 may be subjected to surface treatment, for example, treatment for make the web hydrophilic or treatment for make the web water repellent in appropriate steps of the illustrated process, if necessary. If the first web 111 is provided in the form of film monoaxially stretched along the direction in which this web is fed, formation of the openings by the columnar water streams will be further facilitated. The first web 111 has a thickness of 0.01~0.05 mm and the second web 112 has a basis weight of 5~50 g/m². In the process illustrated in FIG. 6, it is also possible to eliminate the first treating zone 123 and to subject the webs to the high pressure columnar water streams only in the second treating zone 127 so that the composite sheet 102 is formed directly from the first composite web 104 without making the second composite web 107. However, such process is apt to be accompanied with a problem that unacceptably narrow openings and excessively many bridge-like portions may be formed since the effect of the columnar water streams upon the first web will be at most indirect. It should be understood that the composite sheet 102 is subjected to an appropriate drying treatment.

As will be apparent from the foregoing description, the flexible composite sheet according to this invention comprises the fibrous layer and a plurality of thermoplastic synthetic resin lamellae overlying the fibrous layer wherein the fibrous layer is exposed between each pair of the adjacent lamellae and each of the lamellae is formed on its upper surface with the grooves which are contiguous to the fibrous layer extending between the directly opposed side edges of the adjacent lamellae. With such unique arrangement, the composite sheet according to this invention enables, if the composite sheet is used, for example, as the topsheet of the sanitary napkin, menstrual discharge to be smoothly guided along the grooves into the fibrous layer and thereby to be prevented from staying on the upper surfaces of the respective lamellae.

What is claimed is:

1. A flexible composite sheet comprising:

a fibrous layer having upper and tower surfaces; and a plurality of discrete quadrilaterally-shaped thermoplastic synthetic resin lamella film portions that are spaced apart from one another and arranged in an array on the upper surface of the fibrous layer and bonded thereto, each of said plurality of discrete quadrilaterally-shaped thermoplastic synthetic resin lamella film portions having an upper surface with a plurality of grooves formed therein extending between opposite sides thereof.

2. The flexible composite sheet according to claim 1, wherein each of said plurality of discrete quadrilaterally-shaped thermoplastic synthetic resin lamella film portions has a thickness of about 0.001 to 0.05 mm and a width of about 0.03 to 5 mm, and each extend parallel to one another on the upper surface of said fibrous layer in one direction and are spaced apart from one another orthogonally to said one direction by about 0.03 to 1 mm, each of said plurality of discrete quadrilaterally-shaped thermoplastic synthetic resin lamella film portions being formed along side edges thereof extending in said one direction with a plurality of tooth-shaped portions rising from an upper surface thereof.

3. The flexible composite sheet according to claim 1, wherein said plurality of discrete quadrilaterally-shaped thermoplastic synthetic resin lamella film portions have upper surfaces that curve upward between adjacent ones of said plurality of grooves.

4. The flexible composite sheet according to claim 1, wherein lower surfaces of said plurality of discrete quadrilaterally-shaped thermoplastic synthetic resin lamella film portions are bonded to said fibrous layer along said grooves and are spaced apart from said fibrous layer between said grooves.

5. The flexible composite sheet according to claim 1, wherein each of said plurality of grooves has a depth of about 0.001 to 5 mm.

6. The flexible composite sheet according to claim 1, wherein a center-to-center distance between adjacent ones of said grooves is about 0.03 to 10 mm.

7. The flexible composite sheet according to claim 1, wherein adjacent ones of said plurality of discrete quadrilaterally-shaped thermoplastic synthetic resin lamella film portions are connected to one another by bridge portions that extend therebetween.

* * * * *